United States Patent
Ishikawa et al.

(10) Patent No.: US 10,392,259 B2
(45) Date of Patent: Aug. 27, 2019

(54) METHOD FOR MANUFACTURING CALCIUM CARBONATE BLOCK

(71) Applicants: GC CORPORATION, Tokyo (JP); KYUSHU UNIVERSITY, National University Corporation, Fukuoka-shi, Fukuoka (JP)

(72) Inventors: Kunio Ishikawa, Fukuoka (JP); Katsushi Yamamoto, Tokyo (JP)

(73) Assignees: GC CORPORATION, Tokyo (JP); Kyushu University, National University Corporation, Fukuoka-shi, Fukuoka (JP)

(*) Notice: Subject to any disclaimer, the term of this patent is extended or adjusted under 35 U.S.C. 154(b) by 0 days.

(21) Appl. No.: 15/515,470

(22) PCT Filed: Sep. 29, 2015

(86) PCT No.: PCT/JP2015/077513
§ 371 (c)(1),
(2) Date: Mar. 29, 2017

(87) PCT Pub. No.: WO2016/052502
PCT Pub. Date: Apr. 7, 2016

(65) Prior Publication Data
US 2017/0210635 A1 Jul. 27, 2017

(30) Foreign Application Priority Data
Sep. 30, 2014 (JP) .................. 2014-200768

(51) Int. Cl.
*C01F 11/18* (2006.01)
*A61L 27/02* (2006.01)
*A61L 27/56* (2006.01)
*A61L 27/00* (2006.01)

(52) U.S. Cl.
CPC ............. *C01F 11/18* (2013.01); *A61L 27/025* (2013.01); *A61L 27/56* (2013.01); *A61L 27/00* (2013.01); *A61L 2430/02* (2013.01)

(58) Field of Classification Search
CPC ....... A61L 2430/02; A61L 27/56; C01F 11/18
See application file for complete search history.

(56) References Cited

U.S. PATENT DOCUMENTS

| 8,012,218 B2 | 9/2011 | Ishikawa et al. |
| 2006/0225619 A1* | 10/2006 | Ishikawa ............ A61L 27/12 106/690 |
| 2011/0295383 A1 | 12/2011 | Ishikawa et al. |

FOREIGN PATENT DOCUMENTS

| CN | 1809391 A | 7/2006 |
| EP | 1 642 600 A1 | 4/2006 |
| JP | 50-149599 A | 11/1975 |
| JP | 05-237178 A | 9/1993 |
| JP | 08-198659 A | 8/1996 |
| JP | 08-290949 A | 11/1996 |
| JP | 2005-239528 A | 9/2005 |
| JP | 4854300 B2 | 1/2012 |
| WO | 2007/130344 A2 | 11/2007 |

OTHER PUBLICATIONS

Shigeki Matsuyama, et al., "Preparation of carbonated apatite monolith by treatment of calcium carbonate in phosphate solutions", The Journal of the Japanese Society for Dental Materials and Devices, Aug. 25, 2003, p. 406, vol. 22, No. 5.
International Search Report for PCT/JP2015/077513 dated Nov. 10, 2015 [PCT/ISA/210].
Written Opinion for PCT/JP2015/077513 dated Nov. 10, 2015 [PCT/ISA/237].

* cited by examiner

*Primary Examiner* — Stella K Yi
(74) *Attorney, Agent, or Firm* — Sughrue Mion, PLLC

(57) ABSTRACT

An object is to provide a method for manufacturing a calcium carbonate block of no less than 0.1 cm in diameter and thickness, not including any impurities, and able to be employed as a raw material of an artificial bone that requires biosafety: the method includes: (a) shaping a calcium hydroxide block; (b) being exposed to carbon dioxide; and (c) immersing in a carbonate ion containing solution.

2 Claims, No Drawings ns method for manufacturing -->
METHOD FOR MANUFACTURING CALCIUM CARBONATE BLOCK

CROSS REFERENCE TO RELATED APPLICATIONS

This application is a National Stage of International Application No. PCT/JP2015/077513 filed Sep. 29, 2015, claiming priority based on Japanese Patent Application No. 2014-200768 filed Sep. 30, 2014, the contents of all of which are incorporated herein by reference in their entirety.

TECHNICAL FIELD

This invention relates to a method for manufacturing a calcium carbonate block useful as material of an artificial bone.

BACKGROUND ART

In a medical field such as medical science and dentistry, the first choice as a means of restoring a large bone defect or void is autogenous bone grafting onto such a defect or void. However, grafting using bone graft material that can be substituted for an autogenous bone is widely done because invasive surgery has to be done on a healthy part in order to take an autogenous bone, and there is a limit on the amount of a bone to be taken. Mechanical characteristics, biosafety, osteogenic potential and so on, which are similar to those of a in vivo bone are required from this bone graft material.

Bone graft material is categorized as: an allogeneic bone taken out of a dead body; a xenogeneic bone taken out of another animal such as cattle; and a chemically synthesized artificial bone. While an allogeneic bone and a xenogeneic bone may carry a risk of infectious diseases due to contamination by factors originated from another organism, an artificial bone does not carry such a risk, which is superior. Thus, artificial bones have been developed in recent years.

A ceramic artificial bone whose main component is calcium phosphate is known as an artificial bone. Material most studied is hydroxyapatite. Hydroxyapatite is an extremely useful bone graft material because of its osteoconductivity. However, hydroxyapatite is non-bioresorbable material and does not disappear. Thus, hydroxyapatite remains in a body as a foreign body semipermanently. This might cause leakage from a grafted defect, and inflammation due to infection of a graft. Therefore, bioresorbable bone graft material is desired.

Therefore, a ceramic artificial bone consisting of β-tricalcium phosphate (β-TCP), which is bioresorbable material, has been developed (for example, see Patent Literature 1). This artificial bone is superior in bioresorbability, and thus, disappears in the end. However, the mechanism of its resorbence does not depend on that of a living body such as physicochemical solution. Thus, if a bone defect is large or the like, there is a possibility that an artificial bone disappears before the bone is sufficiently ossified.

In contrast, carbonate apatite has been developed in recent years as bone graft material resorbed according to a mechanism of a living body (for example, Patent Literature 2). Carbonate apatite has a composition similar to an in vivo bone, and thus, is resorbed according to a mechanism of a living body. Therefore, it is said that a bone can be repaired with high predictability because bone formation by osteoblast cells and resorbence of bone substitute material by osteoclast cells (remodeling) are properly carried out.

A method of immersing a precursor of calcium carbonate in a phosphate solution is effective as a method for manufacturing carbonate apatite (for example, Patent Literature 2 described above). Here, only carbonate apatite over a certain size, which can have, for example, a granular or block-like shape, can be applied to a living body because it is known that, a living body recognizes, for example, powdery bone graft material under a certain size as foreign bodies, to induce inflammation. On the other hand, for example, large block-shaped carbonate apatite is preferable because capable of a large bone defect or the like.

Large block-shaped calcium carbonate is necessary as a precursor in order to obtain, for example, large block-shaped carbonate apatite. However, calcium carbonate is powdery, and is necessary to be artificially shaped into a block. For example, sintering cannot be employed because calcium carbonate is decomposed if sintering is carried out thereon. Although there is some disclosure of shaping calcium carbonate into a block, such disclosure cannot be employed for a raw material of an artificial bone that requires biosafety. For example, an inorganic filler such as calcium carbonate are bound by an organic and/or inorganic binder to be hardened, to obtain a calcium carbonate block that is generally called cultured marble (for example, see Patent Literature 3). Such a calcium carbonate block cannot be employed because there is a possibility that impurities that might have a bad influence on a human body remain.

In contrast, in Patent Literature 2 described above, powder of calcium hydroxide is compression-molded and the resultant compressed body is subjected to carbonation under a stream of carbon dioxide with a relative humidity of 100% to obtain calcium carbonate blocks. According to this method, calcium carbonate blocks can be obtained without a problem about biosafety because safe calcium hydroxide according to Japanese Pharmacopoeia or the like is available, and the powders bond with each other at the same time of the carbonation, to give the blocks strength.

CITATION LIST

Patent Literature

Patent Literature 1: H5-237178A
Patent Literature 2: JP 4854300B2
Patent Literature 3: JP H8-290949A

SUMMARY OF INVENTION

Technical Problem

However, the method of Patent Literature 2 is not practical because the speed of carbonation is slow. For example, it needs a long time (for example, 168 hours) to completely carbonate a compressed body having a relatively small size of no less than 0.1 cm in diameter and thickness. Further, the center part is not completely carbonated even if a longer time (for example, 672 hours) has passed in case of the compressed body of no less than 1 cm in diameter and thickness. Therefore, there is a problem that calcium hydroxide remains at the center part of an obtained calcium carbonate block, thereby the center part of the block does not become carbonate apatite when the block is made to become carbonate apatite in the next process.

An object of the present invention is to provide a method for manufacturing a calcium carbonate block of no less than 0.1 cm in diameter and thickness, not including any impurities, and able to be employed as a raw material of an artificial bone that requires biosafety.

Solution to Problem

As a result of the intensive studies of the inventors and so on to solve the above problems, they found that: calcium hydroxide is shaped into a block and exposed to carbon dioxide, to partially carbonate the surface of the block, and then is immersed in carbonate ion containing solution; even if calcium hydroxide, which does not react, remains, this remaining calcium hydroxide reacts with carbonate ions in the solution, to produce calcium carbonate; thus, a calcium carbonate block of no less than 0.1 cm in diameter and thickness, not including any impurities, is surely obtained. Then, they completed the present invention.

That is, a first embodiment of the present invention is: a method for manufacturing a calcium carbonate block comprising:
(a) shaping a calcium hydroxide block;
(b) exposing carbon dioxide; and
(c) immersing in a carbonate ion containing solution.

In addition, a second embodiment of the present invention is:
a method for manufacturing a calcium carbonate block comprising:
(a) shaping a calcium hydroxide block;
(b) being exposed to carbon dioxide; and
(c) immersing in a carbonate ion containing solution; and further comprising:
(d) mixing a pore-forming substance; and
(e) forming a pore.

Advantageous Effects of Invention

The method for manufacturing a calcium carbonate block according to the present invention is a method for manufacturing a calcium carbonate block able to be employed as a raw material of an artificial bone that requires biosafety, and is an outstanding method for manufacturing a calcium carbonate block, capable of manufacturing a calcium carbonate block of no less than 0.1 cm in diameter and thickness, and not including any impurities.

DESCRIPTION OF EMBODIMENTS

Hereinafter the embodiments of the present invention will be described in detail.

(a) a step of shaping a calcium hydroxide block is a step of shaping calcium hydroxide that is a precursor of calcium carbonate into a block. Generally, calcium hydroxide is available in a shape of powder. Thus, a compression mold is filled with calcium hydroxide powder, to compress the powder using a compression molding machine, which makes it possible to shape the powder into a block. The strength of a block to be obtained can be changed by controlling molding pressure. Molding pressure ranging from 10 to 300 kg/cm$^2$ is preferable.

The shape of a block can be also realized by, after mixing calcium hydroxide powder with a solvent such as water, removing the solvent.

A size of the shaped block is, preferably, 0.1 cm to 50 cm in diameter and 0.1 cm to 5 cm in thickness. Especially, the size of 3 cm to 10 cm in diameter and 1 cm to 2 cm in thickness is preferable. Examples of a shape of the block include a round column, a rectangular parallelepiped and a flat plate.

Non-limiting calcium hydroxide can be used as a raw material as long as not including any impurities. Calcium hydroxide according to the Japanese Pharmacopoeia is especially preferable because safety is secured. It is also possible to mix calcium hydroxide with another substance to be shaped into a block. Examples of this substance include hydroxyapatite, β-tricalcium phosphate and calcium sulphate.

Prior to (a) the step of shaping a calcium hydroxide block, (d) a step of mixing a pore-forming substance can be included. (d) the step of mixing a pore-forming substance is a step of mixing a substance that is soluble in a specific solvent (pore-forming substance) with calcium hydroxide that is a raw material. Including this (d) step of mixing a pore-forming substance and (e) a step of forming a pore, which will be described later, a porous calcium carbonate block where pores are distributed all over can be obtained. The mixing ratio of this calcium hydroxide to a pore-forming substance ranges preferably from 2:1 to 1:2. A size of the pore-forming substance is preferably 50 µm to 300 µm. A specific solvent can be water, and a substance soluble in water can be sodium chloride, trisodium citrate or the like.

(b) a step of being exposed to carbon dioxide is a step of being exposed to a calcium hydroxide block that is obtained in (a) the step of shaping a calcium hydroxide block to carbon dioxide, to be carbonated. According to this step, calcium hydroxide react with carbon dioxide, to produce calcium carbonate. Whereby, a partial calcium carbonate block at least a part of which is calcium carbonate is obtained. However, when a size of the block is large, or when compression pressure upon shaping the block is high, there is a possibility that calcium hydroxide remains in, especially, the center part even if it takes long for the reaction time (for example, 672 hours).

Examples of a method for realizing a carbonation atmosphere include a method of using a carbonic acid incubator. While carbonation conditions depend on a size of the block, compression pressure and so on, carbonation conditions such as the concentration of carbonic acid gas, a relative humidity and a temperature can be properly controlled by using a carbonic acid incubator. Preferable carbonation conditions are: 5% to 20% of the concentration of carbonic acid gas, 90% to 100% of a relative humidity and 20° C. to 40° C. of a temperature. Time for carbonation is, for example, 1 hour to 168 hours.

(c) a step of immersing in a carbonate ion containing solution is a step of immersing the partial calcium carbonate block obtained in (b) the step of being exposed to carbon dioxide, in a carbonate ion containing solution. According to this step, calcium hydroxide remaining in the partial calcium carbonate react with carbonate ions, to produce calcium carbonate. That is, a calcium carbonate block not including any impurities is obtained. In this step, because a carbonate ion containing solution directly reacts with calcium hydroxide, it is possible to completely carbonate calcium hydroxide a part of which cannot be carbonated in (b) the step of being exposed to carbon dioxide, and to carry out carbonation faster than (b) the step of being exposed to carbon dioxide. Immersion time is, for example, 1 hour to 168 hours.

Examples of a method for preparing a carbonate ion containing solution include a method of dissolving a carbonate ion supplying substance other than a method of dissolving carbonic acid gas in water. Non-limiting carbonate ion supplying substances can be used as long as not including impurities and being soluble in water. A carbonate ion supplying substance according to the Pharmacopoeia is especially preferable because safety is secured. Examples of such a substance include sodium carbonate, sodium hydrogencarbonate, potassium carbonate, potassium hydrogencarbonate, ammonium carbonate and ammonium hydrogencarbonate. A higher temperature of a solution is desirable because carbonation is more effective and progress of reaction is faster. More specifically, no less than 20° C. is desirable. The solution can be prepared to have a temperature of the boiling point or over, using a reflux apparatus, a hydrothermal reaction apparatus that can apply pressure, etc. In view of the simplicity of the apparatus, 20° C. to 95° C. is preferable, and 60° C. to 90° C. is more preferable. While the concentration of carbonate ions in the solution is not especially specified, a higher concentration is desired because carbonation is more effective and progress of reaction is faster. When a carbonate ion supplying substance is used, the concentration depends on the solubility of the substance in water. In view of a cleaning step or the like after the reaction, the concentration of carbonate ions is desirably 0.5 mol/L to 1.5 mol/L.

In a case where (d) the step of mixing a pore-forming substance described above is included prior to (a) the step of shaping a calcium hydroxide block, (e) a step of forming a pore can be included after (b) the step of being exposed to carbon dioxide or (c) the step of immersing in a carbonate ion containing solution. (e) the step of forming a pore is a step of dissolving the substance soluble in a specific solvent, which is mixed in (d) the step of mixing a pore-forming substance, in the specific solvent. This step makes it possible to obtain a porous calcium carbonate block where pores are distributed all over. The specific solvent can be water, and the substance soluble in water can be sodium chloride, trisodium citrate or the like.

The calcium carbonate block obtained by the method for manufacturing a calcium carbonate block according to the present invention is a calcium carbonate block not including impurities as described above. Thus, if this is immersed in a phosphate solution to react, a carbonate apatite block of a large size which does not include impurities is obtained. Including (d) the step of mixing a pore-forming substance and (e) the step of forming a pore makes it possible to obtain a porous calcium carbonate block, to form a porous carbonate apatite block as well.

In the present invention, (b) the step of being exposed to carbon dioxide is carried out and thereby, at least an outer surface of the calcium hydroxide block obtained in (a) the step of shaping a calcium hydroxide block becomes calcium carbonate, and generated calcium carbonate molecules are in a state of being chemically bonded to each other organically. Whereby, a calcium carbonate block can be obtained without decay even if (c) the step of immersing in a carbonate ion containing solution is carried out. In contrast, in a case where (c) the step of immersing in a carbonate ion containing solution is carried out without carrying out (b) the step of being exposed to carbon dioxide, calcium hydroxide molecules in the calcium hydroxide block obtained in (a) the step of shaping a calcium hydroxide block are just pressed and hardened, and not chemically bonded with each other. Thus, if this is immersed in a carbonate ion containing solution, the block easily decays. Thus, a calcium carbonate block cannot be obtained.

Employing the above described technical idea makes it possible to obtain a calcium carbonate block not including any impurities by covering at least the outer surface of the block with calcium carbonate in (b) the step of being exposed to carbon dioxide and rapidly completing carbonation of its inside in (c) the following step of immersing in a carbonate ion containing solution, especially even if the block is no less than 1 cm in diameter and thickness, which is relatively large and difficult to be completely carbonated with conventional methods. Therefore, the present invention is outstandingly effective.

Hereinafter concrete examples will be given and the method for manufacturing a calcium carbonate block according to the present invention will be described. The present invention is not limited to the examples.

EXAMPLES

Example 1

Calcium hydroxide according to the Japanese Pharmacopoeia of 10 g underwent uniaxial pressing at 50 kg/cm$^2$ of axial force using a circular metal mold of 30 mm in diameter, to shape a compressed body of calcium hydroxide. The resultant compressed body of calcium hydroxide was left to stand in a carbonic acid incubator of the concentration of carbon acid gas: 5%, a relative humidity: 100% and a temperature: 30° C., to be carbonated thereon for 24 hours. A resultant partial calcium carbonate block was immersed in a sodium hydrogen carbonate solution of 1 mol/L at 80° C., and after 48 hours, underwent washing and drying. A resultant calcium carbonate block was divided, and a phenolphthalein solution was dropped on an exposed center part thereof. As a result, the center part was white as calcium carbonate was, and no coloration was observed. Whereby, it was confirmed that unreacted calcium hydroxide did not remain.

Example 2

Calcium hydroxide according to the Japanese Pharmacopoeia of 5 g and sodium chloride according to the Japanese Pharmacopoeia of 5 g, whose average particle diameter was 300 μm, were uniformly mixed using a V-type mixer. The resultant mixed powder underwent uniaxial pressing at 100 kg/cm$^2$ of axial force using a circular metal mold of 30 mm in diameter, to shape a compressed body of calcium hydroxide/sodium chloride. The resultant compressed body of calcium hydroxide/sodium chloride was left to stand in a carbonic acid incubator of the concentration of carbon acid gas: 20%, a relative humidity: 100% and a temperature: 30° C., to be carbonated for 24 hours. A resultant partial calcium carbonate/sodium chloride block was subjected to displacement washing with distilled water five times, to remove sodium chloride. A resultant porous partial calcium carbonate block was immersed in an ammonium carbonate solution of 0.5 mol/L at 100° C., and after 48 hours, underwent washing and drying. A resultant porous calcium carbonate block was divided, and a phenolphthalein solution was dropped on an exposed center part thereof. As a result, the center part was white as calcium carbonate was, and no coloration was observed. Whereby, it was confirmed that unreacted calcium hydroxide did not remain.

Comparative Example 1

After a compressed body of calcium hydroxide was shaped under the same conditions of Example 1, carbonation using a carbonic acid incubator was carried out thereon, to obtain a partial calcium carbonate block. However, immersion in a sodium hydrogen carbonate solution was not carried out after that. The resultant partial calcium carbonate block was divided, and a phenolphthalein solution was dropped on an exposed center part thereof. As a result, while a portion outside the center part was white as it had been and no coloration was observed, the center part was colored red. Whereby, it was confirmed that unreacted calcium hydroxide remained.

The invention claimed is:

1. A method for manufacturing a calcium carbonate block comprising:
   (a) shaping a block of calcium hydroxide;
   (b) exposing the block to carbon dioxide gas;
   (c) immersing the block in a solution containing carbonate ions; and
   after the immersing step, washing with water and drying the block,
   wherein all of the calcium hydroxide of the block is converted to calcium carbonate after the drying.

2. The method for manufacturing a calcium carbonate block according to claim 1, the method further comprising:
   (d) mixing a pore-forming substance; and
   (e) forming a pore.

* * * * *